United States Patent
He

(10) Patent No.: US 10,294,452 B2
(45) Date of Patent: May 21, 2019

(54) LYSIS, EXTRACTION AND PURIFICATION OF ADENO-ASSOCIATED VIRUS AND ADENOVIRUS FROM HOST CELLS

(71) Applicant: Dao-Yao He, Hercules, CA (US)

(72) Inventor: Dao-Yao He, Hercules, CA (US)

( * ) Notice: Subject to any disclaimer, the term of this patent is extended or adjusted under 35 U.S.C. 154(b) by 0 days.

(21) Appl. No.: 15/359,498

(22) Filed: Nov. 22, 2016

(65) Prior Publication Data

US 2018/0143117 A1    May 24, 2018

(51) Int. Cl.
*C12N 7/02* (2006.01)
*C12N 1/06* (2006.01)

(52) U.S. Cl.
CPC ............. *C12N 1/06* (2013.01); *C12N 7/02* (2013.01)

(58) Field of Classification Search
None
See application file for complete search history.

(56) References Cited

U.S. PATENT DOCUMENTS

| 6,093,570 A * | 7/2000 | Ferrari | C07K 14/005 |
| | | | 435/320.1 |
| 6,566,118 B1 * | 5/2003 | Atkinson | C07C 2/32 |
| | | | 435/235.1 |
| 7,704,721 B2 * | 4/2010 | Wright | C12N 7/00 |
| | | | 435/239 |
| 2002/0127582 A1 | 9/2002 | Atkinson | |
| 2005/0042740 A1 * | 2/2005 | Qu | C12N 7/00 |
| | | | 435/239 |
| 2007/0275449 A1 * | 11/2007 | Wu | C12N 7/00 |
| | | | 435/239 |

FOREIGN PATENT DOCUMENTS

| EP | 3323895 | 5/2018 |
| WO | WO-1998/022588 | 5/1998 |
| WO | WO-2003/097797 | 11/2003 |
| WO | WO-2005/080556 | 9/2005 |

OTHER PUBLICATIONS

Guo et al., "Rapid and simplified purification of recombinant adeno-associated virus," J Virol Methods 183(2): 139-146 (2012).*
Qu et al., "Separation of adeno-associated virus type 2 empty particles from genome containing vectors by anion-exchange column chromatography," Journal of Virological Methods 140: 183-192 (2007).*

(Continued)

*Primary Examiner* — M Franco G Salvoza
(74) *Attorney, Agent, or Firm* — Sheppard Mullin Richter & Hampton LLP

(57) ABSTRACT

The present disclosure provides compositions and methods for extracting viral particles of a recombinant adeno-associated virus (AAV) or an adenovirus (AdV) from a sample comprising cells enclosing the viral particles. The method can include lysing the cells with the addition of an alkaline lysis solution to the sample such that the sample comprises compound(s) buffering pH value about 9.0 to about 11.5 and about 0.1% to about 1% of a detergent precipitating host cell proteins by adding a salting solution to the sample such that the sample comprises about 0.5 M to about 2.0 M of a salt and has a pH of about 4.0 to about 7.0.

10 Claims, 9 Drawing Sheets

Specification includes a Sequence Listing.

(56) References Cited

OTHER PUBLICATIONS

Lock et al., "Rapid Simple, and Versatile Manufacturing of Recombinant Adeno-Associated Viral Vectors at Scale," Human Gene Therapy 21: 1259-1271 (2010).*
Machida , "Viral Vectors for Gene Therapy: Methods and Protocols," Humana Press (Year: 2003).*
Becker et al., "Use of Recombinant Adenovirus for Metabolic Engineering of Mammalian Cells," Methods in Cell Biology, vol. 43 (Year: 1994).*
European Search Report for EP 17202840 dated Feb. 22, 2018, 10 pages.

* cited by examiner

LYSIS, EXTRACTION AND PURIFICATION OF ADENO-ASSOCIATED VIRUS AND ADENOVIRUS FROM HOST CELLS

SEQUENCE LISTING

The instant application contains a Sequence Listing which has been filed electronically in ASCII format and is hereby incorporated by reference in its entirety. Said ASCII copy, created on Feb. 6, 2017, is named 52VP-246742-US_SL.txt and is 1,375 bytes in size.

BACKGROUND

Since "virus-like" particles were first discovered in adenovirus (AdV) preparations, adeno-associated virus (AAV) has been characterized and developed in the last 50 years as a potent viral vector to deliver genes in vitro in cultured cells and in vivo in animal models. AAV is a small, "naked" virus containing a single-stranded DNA genome of approximately 4.7 kb, consisting of two inverted terminal repeats (ITRs) that are capable of forming T-shape secondary structure and acting as origins of genome replication, one rep region that encodes four overlapping replication proteins, Rep78, Rep68, Rep52, and Rep40, and one cap region that encodes three structural proteins, VP1, VP2, and VP3. Naturally isolated serotypes 1-9 of the AAV viruses share the genomic structure although these serotypes may display different tissue tropism. Numerous investigations have revealed their attractive features including nonpathogenicity, efficient transduction and stable expression, thus laying foundations for recombinant AAV vectors for use as one of the most successful gene delivery vehicles.

Production of recombinant AAV vectors (rAAV) is traditionally achieved by transfection of human-derived HEK293 cells with a rAAV viral vector and a packaging construct in the presence of auxiliary viruses such as adenoviruses (AdV) that provide the helper function. After identification of AdV regions required for AAV vector packaging, a helper virus-free method was established using a constructed helper plasmid acting as auxiliary viruses. Therefore, a helper-free system is a triple transfection protocol consisting of three plasmids, which system is widely used in research and drug development. In addition, development of baculovirus expression vectors provides another method to produce rAAV viruses in insect sf9 cells. These different technologies are shown to be able to produce sufficient quantities of rAAV viruses for use in laboratories and clinical trials.

For purification of all of the different AAV serotypes, the viral particles are first released from the packaging cells using 3-4 freeze/thaw cycles, a conventional extraction method. In most purification protocols established to date, cesium chloride-(CsCl) and iodixanol-based density gradient ultracentrifugation is a central step. Although the gradient purification is useful in laboratory settings, it has raised concerns for clinical applications. Such concerns, in general, relate to (1) significant reduction of infectivity, (2) gradient-associated health risks, (3) gradient-associated toxicity, and (4) cumbersome procedures.

More recently, affinity and ion exchange chromatography have been tested for AAV particle purification. Such technologies, however, are associated with high cost and low scalability, or suffer from difficulties in separating viral particles from empty particles. Either affinity or ion exchange chromatography alone is unable to produce high purity of AAV viruses.

SUMMARY

The present disclosure, in certain embodiments, provides methods to lyse, extract and purify AAV or AdV viral particles from host cells. The methods entail lysing the cells with an alkaline lysis solution comprising pH-buffering compound(s) or reagent(s) and a preferably mild detergent, followed by precipitating and removing the majority of host cell proteins with a salting solution which preferably comprises a salt, under a relatively acidic condition. The extracted viral solution can be desalted and enriched with certain polyethylene glycol (PEG) and further purified by chromatography.

In accordance with one embodiment of the present disclosure, provided is a method of extracting viral particles of a recombinant adeno-associated virus (AAV) or an adenovirus (AdV) from a sample comprising cells enclosing the viral particles. In some embodiments, the method comprises lysing the cells by the addition of an alkaline lysis solution to the sample such that the sample comprises about 0.1% to about 1% of a detergent and has a pH of about 9.0 to about 11.5. In one embodiment, the method further comprises precipitating host cell proteins by adding a salting solution to the sample such that the sample comprises about 0.5 M to about 2.0 M of a salt and has a pH of about 4.0 to about 7.0.

In some embodiments, the viral particles are of any one of AAV serotypes 1-11 or any one of AdV species A-G. In some embodiments, the detergent is a mild detergent. In some embodiments, the detergent is selected from the group consisting of deoxycholate, octyl thioglucoside, octyl glucoside, dodecyl maltoside, octyl thioglucoside, octyl glucoside, alkyl Sulfates, Polysorbate 20 (Tween-20), Tergitol-type NP-40 and the combinations thereof. In some embodiments, the detergent is deoxycholate. In some embodiments, the detergent is deoxycholate and sodium dodecyl sulfate (SDS).

In some embodiments, the alkaline lysis solution has a pH of about 9.0 to about 11.5 and comprises, in addition to the detergent, one or more reagents selected from the group consisting of N-cyclohexyl-3-aminopropanesulfonic acid (CAPS), glycine/sodium, glycine/potassium, sodium carbonate, potassium carbonate, sodium phosphate, potassium-phosphate and combinations thereof. In some embodiments, the sample, following addition of the alkaline lysis solution, comprises about 0.1% to about 1.0% of the detergent.

In some embodiments, the salt is selected from the group consisting of sodium acetate, potassium acetate, sodium phosphate and combinations thereof. In some embodiments, the salting solution does not include an ammonium salt.

In some embodiments, the method further comprises precipitating the viral particles by adding a precipitation solution to the sample such that the sample comprises about 5% to about 12% of a polyethylene glycol (PEG). In some embodiments, the PEG has an average molecular weight of about 3000 to about 10000.

In some embodiments, the method further comprises subjecting the precipitated viral particles to chromatography. In some embodiments, the chromatography is silica-based chromatography, resin chromatography or ion exchange chromatography columns.

In some embodiments, the method does not include the use of an organic solvent. In some embodiments, the method does not include the use of ultracentrifugation. In some embodiments, the method does not include extraction by freeze-thaw cycles. In some embodiments, the method does not include the use of affinity chromatography.

Also provided are formulations and compositions comprising adeno-associated viruses (AAV) or recombinant adenoviruses (AdV) purified with any method of the above embodiments.

Provided in another embodiment of the present disclosure is a preparation of viral particles of a recombinant adeno-associated virus (rAAV) or an recombinant adenovirus (rAdV), extracted and purified from a sample of cells enclosing the viral particles, comprising at least 1013 of the particles per milliliter (ml), wherein the preparation contains at least 1010 transducing units (TU) per 1013 of the particles; contains less than 1/10,000 host cell proteins relative to the particles (w/w); and does not contain detectable cesium chloride (CsCl) or iodixanol. In some embodiments, no more than 1/10,000 of the viral particles are empty particles.

DETAILED DESCRIPTION

Definitions

Figure 1:
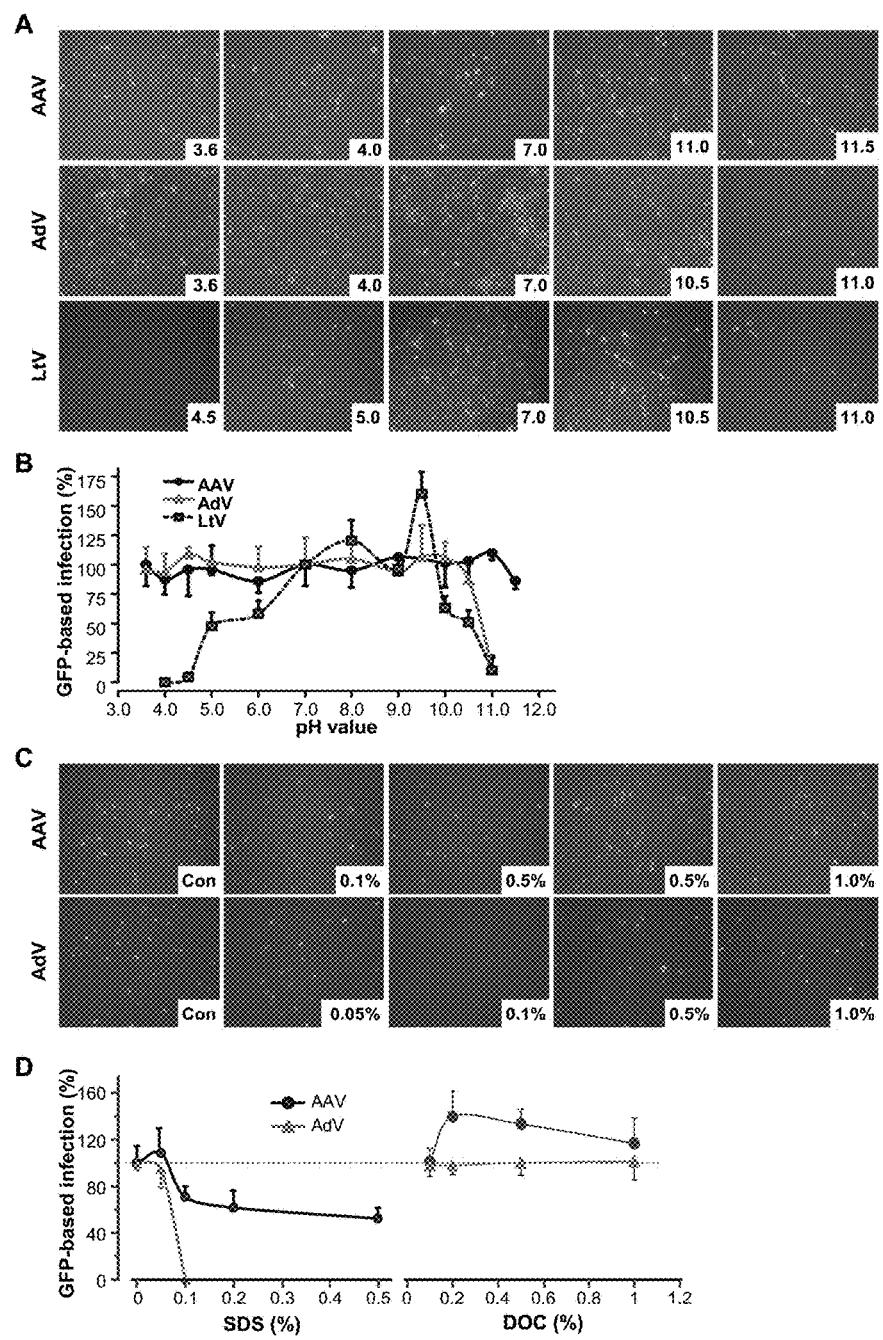
FIG. 1 with panels A-D presents data demonstrating the tolerance of adeno-associated virus (AAV) and adenovirus (AdV) to ranged pH values and to detergents to establish the foundation of development of lysis solutions used for lysis of their packaging cells. (A, B) AAV virus was packaged by transfection of GFP-containing AAV viral vector and packaging plasmids into HEK293 cells. GFP-containing AdV virus was amplified by infection of HEK293 cells. Lentivirus (LtV) was packaged by transfection of GFP-containing lentiviral vector and packaging plasmids into 293T cells, used for comparison. The viruses used here all were collected from cultured medium of their packaging cells using 8% PEG8000, suspended in PBS and mixed with an equal volume of the pH solutions as indicated. After 2 hours incubation at room temperature, the viral mixtures were used for infection in HEK293 cells. GFP-expressed cells were photographed and counted 3-4 days post infection. Images of GFP cells shown are representatives of photos (A). GFP cell numbers were analyzed and shown in the scatter chart that is expressed as mean percentage±SD of GFP cell numbers, n=6 (B). (C, D) AAV or AdV viruses were prepared as described above, mixed with an equal volume of different concentrations of detergents, sodium dodecyl sulfate (SDS) or sodium deoxycholate (DOC), as indicated and incubated for 2 hours at room temperature before infection as described above, n=5.

The following description sets forth exemplary embodiments of the present technology. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

Conventional methods for the extraction and purification of AAV and AdV particles entail the use of freeze/thaw cycles followed with density gradient ultracentrifugation. In some methods, affinity or ion exchange chromatography is not employed to improve purity of the final product. Such methods typically result in reduced infectivity of the viruses, accompanied by poor recovery. Moreover, for preclinical or clinical use of the viruses, the gradient-associated health toxicity can be a significant concern.

One embodiment of the present disclosure provides a method of extracting and purifying AAV and AdV particles with improved recovery of the viral particles with greater infectivity. Also, in this method, the freeze/thaw cycles and density gradient ultracentrifugation are not required. The new method is easier to implement and readily scalable. As further detailed below, one embodiment of the method includes lysing the cells packaged with the viruses with an alkaline lysis solution followed by precipitating and removing a majority of host cell proteins with a salt solution. Furthermore, the extracted viral particles can be precipitated with polyethylene glycol (PEG) and purified by chromatography. The methods disclosed herein are suitable for all different serotypes and species of AAV (e.g., adeno-associated virus serotypes 1-12) or AdV (adenovirus species A-G with their respective serotypes) or other "naked" viruses within cells after packaged.

Cell Lysis

In accordance with one embodiment of the disclosure, cells that enclosing AAV or AdV viruses are lysed with an alkaline lysis solution. Preferably, the lysis solution contains compound(s) or reagent(s) that are buffering a pH of about 9.0 to about 11.5. The lysis solution can also include a detergent which is preferably a mild detergent or a detergent that contributes to cell lysis but does not decrease the viral activities.

An "alkaline lysis solution" or more generally "lysis solution", as used herein, refers to a solution that contains compound(s) or reagent(s) that maintain a pH higher than 7.0, or alternatively higher than 7.5, 8.0, 8.5, or 9.0. The alkaline lysis solution can also include a detergent that is useful for breaking up cells. The detergent is preferably a mild detergent such as deoxycholate, octyl thioglucoside, octyl glucoside, dodecyl maltoside, octyl thioglucoside, octyl glucoside, alkyl Sulfates, polysorbate 20 (Tween-20), Tergitol-type NP-40, or the mixtures thereof.

The pH and ingredients of the lysis solution can be determined based on the desired pH and final concentrations of the ingredients in the cell sample once the lysis solution is added to the sample. In one embodiment, upon addition of the lysis solution to the cell sample, the pH of the sample is preferably at least 8.0, or alternatively at least 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4 or 11.5. In another embodiment, the pH of the sample is not higher than 12.0, or alternatively not higher than 11.9, 11.8, 11.7 or 11.6. In some embodiments, the pH of the sample is from about 8.5 to about 12.0, or from about 9.0 to about 12.0, or from about 9.0 to about 11.5, or from about 8.5 to about 11.5, or from about 9.0 to about 11.0, or from about 9.5 to about 12.0, or from about 9.5 to about 11.5, or from about 9.5 to about 11, or from about 9.5 to about 10.5, or from about 9.5 to about 10.0, or from about 10.0 to about 12.0, or from about 10.0 to about 11.5, or from about 10.0 to about 11.0, or from about 10.0 to about 10.5, without limitation. The pH of the lysis solution can be achieved or adjusted with a compound or reagent, like a base, having a concentration from about 0.05 M to about 0.2 M, for instance.

In some embodiments, the sample has a final concentration of the detergent at about 0.1% to about 1%, and thus the concentration of the detergent in the lysis solution can be higher than this. In one embodiment, the final concentration of the detergent in the sample is at least about 0.1%, or alternatively at least about 0.2%, 0.3%, 0.4%, 0.5%, 0.6%, 0.7%, 0.8%, or 0.9%. In another embodiment, the final concentration of the detergent in the sample is not greater than about 1.5%, or alternatively not greater than about 1.4%, 1.3%, 1.2%, 1.1%, 1.0%, 0.9%, 0.8%, 0.7%, 0.6% or 0.5%. In some embodiments, the final concentration of the detergent in the sample is from about 0.1% to about 1.5%, from about 0.1% to about 1.0%, from about 0.2% to about 0.9%, from about 0.3% to about 0.8%, or from about 0.4% to about 0.7%, without limitation.

The detergent used is preferably mild unlike strong detergents such as Triton X-100 or sodium dodecyl sulfate (SDS). Non-limiting examples of detergents suitable for use here include deoxycholate, octyl thioglucoside, octyl glucoside, dodecyl maltoside, octyl thioglucoside, octyl glucoside, alkyl Sulfates, polysorbate 20 (Tween-20), and Tergitol-type NP-40. In one embodiment, the detergent used is deoxycholate, such as sodium deoxycholate (DOC).

In addition to the detergent, the lysis solution can also include compound ingredients such as N-cyclohexyl-3-aminopropanesulfonic acid (CAPS), glycine/sodium, glycine/potassium, sodium carbonate, potassium carbonate, sodium phosphate, potassium-phosphate or the combinations thereof.

Salting Precipitation

It is discovered herein that the cell lysis methods disclosed here, without the need of freeze/thaw cycles, can achieve fairly complete lysis of the cells while maintaining high infectivity of the viruses. Such a lysed viral sample can then be subject to a salting precipitation process which removes a majority of the contaminating host cell proteins.

The salting precipitation step of the process, in one embodiment, includes the addition of a salting solution that has a neutral or acidic pH (e.g., about 3.5 to about 7.0) and includes a salt at a concentration that is at least 0.5 M. A "salting solution" as used herein refers to a solution with the desired pH and salt at a suitable concentration as disclosed herein. Like for the lysis solution, the pH and salt concentration of the salting solution can be determined based on the desired pH and salt concentration in the viral sample and the starting condition of the sample before the salting solution is added.

In one embodiment, the pH of the viral sample, upon addition of the salting solution, is not higher than about 7.0, or alternatively not higher than about 6.9, 6.8, 6.7, 6.6, 6.5, 6.4, 6.3, 6.2, or 6.1. In another embodiment, the pH of the viral sample, upon addition of the salting solution, is higher than about 4.0, or alternatively higher than about 4.1, 4.2, 4.3, 4.4, 4.5, 4.6, 4.7, 4.8, 4.9, 5.0, 5.1, 5.2, 5.3, 5.4, or 5.5. In some embodiments, the pH of the viral sample, upon addition of the salting solution, is from about 3.5 to about 7.0, from about 3.6 to about 7.0, from about 4.1 to about 6.5, from about 4.5 to about 6.5, from about 5.0 to about 7.0, from about 5.0 to about 6.5, or from about 5.0 to about 6.0.

The salt or salts used in the salting solution can be selected from one or more of the following: sodium acetate, potassium acetate, or sodium phosphate, without limitation. Final concentration of the salt in the viral sample can be from about 0.5 M and up. In one embodiment, the final concentration of the salt or salts is at least 0.5 M, or alternatively at least about 0.6 M, 0.7 M, 0.8 M, 0.9 M, 1.0 M, 1.1 M, 1.2 M, 1.3 M, 1.4 M, or 1.5 M. In one embodiment, the final concentration of the salt or salts is not greater than about 3.0 M, 2.5 M, 2.0 M, 1.9 M, 1.8 M, 1.7 M, 1.6 M, 1.5 M, 1.4 M, 1.3 M, 1.2 M, 1.1 M, or 1.0 M. In some embodiments, the final concentration of the salt or salts is from about 0.5 M to about 3.0 M, from about 0.5 M to about 2.5 M, from about 0.5 M to about 2.0 M, from about 0.5 M to about 1.5 M, from about 0.5 M to about 1.0 M, from about 1.0 M to about 1.5 M, from about 1.0 M to about 2.0 M, or from about 1.0 M to about 2.5, without limitation.

Once the salting solution is added to the viral sample, the majority of host cell proteins can be precipitated and removed from the sample by centrifugation, while the viral particles stay in the supernatant, which can be further purified.

Viral Particle Precipitation and Further Purification

The salting step can remove a majority of the proteins from the sample resulting in viral particles enriched in the sample with little protein contamination. Such a sample can be further purified as needed, just as removing the salt in the sample. In one embodiment, the sample is mixed with a precipitation solution that includes a polyethylene glycol (PEG) at a suitable concentration.

The term "precipitation solution" as used herein generically refers to a solution that includes polyethylene glycol (PEG) which, when added to a viral sample, is able to precipitate viral particles. The molecular weight of the PEG is typically from about 3000 to about 15000, or preferably from about 3000 to about 10000. The concentration of the PEG in the precipitation solution is, in one embodiment, at least about 5%. Like for the lysis solution and the salting solution, the concentration of the PEG in the precipitation solution can be determined by the desired PEG concentration in the viral sample upon addition of the precipitation solution in the viral sample.

In one embodiment, the final PEG concentration in the viral sample is at least 5%, or alternatively at least about 6%, 7%, 8%, 9%, 10%, 11% or 12%. In another embodiment, the final PEG concentration in the viral sample is not greater than 15%, or alternatively not greater than 14%, 13% or 12%.

The PEG in the viral sample can precipitate the viral particles which can then be resuspended in a suitable solution.

In one embodiment, the viral sample or resuspended viral particles can be subject to chromatography. Non-limiting examples of chromatography include silica-based chromatography, resin chromatography or ion exchange chromatography columns. Conditions for using the chromatography can be set with conventional knowledge in the art.

The lysis, extraction and purification processes described here, in some embodiment, do not require (but do not exclude) certain techniques commonly used in the art. For instance, in some conventional methods, organic solvents are employed for lysing the cells or degrading proteins. No organic solvents, however, are required by the current technology.

Another commonly used method includes freeze/thaw cycles, which are also not required by the present disclosure technology. Yet another method includes ultracentrifugation, which typically employs a gradient made of cesium chloride (CsCl) or iodixanol. Ultracentrifugation or the associated gradient reagents are also not required in the present technology. Also not required is affinity chromatography, in some embodiments.

Purified Viral Compositions

Viral particles that are prepared by methods of any embodiment of the disclosure are also provided. It is readily appreciated that in addition to the improved efficiency of viral extraction and purification of the present technology, the end product of the technology is also superior to what can be obtained with the conventional technologies.

For instance, since the present technology does not require ultracentrifugation, the end product would necessarily not contain any contamination of the gradients, such as cesium chloride (CsCl) or iodixanol.

Also, superior to the affinity chromatography method which is not effective in removing empty viral particles from viruses, the end product of the present technology would contain a much lower amount of empty particles. In one embodiment, therefore, the end product contains fewer than 1 empty particle per 10,000 viral particles, or alternatively fewer than 1 empty particle per 20,000, 50,000, 100,000, 500,000, $10^6$, $10^7$, $10^8$, $10^9$, or $10^{10}$ viral particles.

Another difference between the product of the present process and those made by conventional technologies is that the present product has less protein contamination. In one embodiment, the end product contains less than about 1/10,000 (w/w) host cell proteins over the total amount of the viral particles, or alternatively less than about 1/20,000, 1/50,000, 1/100,000, 1/500,000, or 1/1,000,000 (w/w) host cell proteins.

Yet another advantage of the present technology is that the purified viruses retain greater infectivity as compared to what has been done in the prior art. In one embodiment, for each $10^{13}$ of the particles in a prepared sample, there are at least $10^{10}$ transducing units of active viruses. In another embodiment, for each $10^{13}$ of the particles in a prepared sample, there are at least $1 \times 10^9$, $2 \times 10^9$, $5 \times 10^9$, $2 \times 10^{10}$, $5 \times 10^{10}$, $1 \times 10^{11}$, $2 \times 10^{11}$, $5 \times 10^{11}$, or $1 \times 10^{12}$ transducing units of viruses.

Methods and Compositions

Adeno-associated virus (AAV) is a small virus which infects humans and some other primate species. AAV is not currently known to cause disease. The virus causes a mild immune response, lending further support to its apparent lack of pathogenicity. Gene therapy vectors using AAV can infect both dividing and quiescent cells and persist in an extrachromosomal state without integrating into the genome of the host cell, although in the native virus some integration of virally carried genes into the host genome does occur. These features make AAV an attractive candidate for creating viral vectors for gene therapy, and for the creation of isogenic human disease models.

The best studied AAV serotype is serotype 2. Serotypes 2, 3, 5, and 6 were discovered in human cells, AAV serotypes 1, 4, and 7-11 in nonhuman primate samples. There have been 11 AAV serotypes described. AAV capsid proteins contain 12 hypervariable surface regions, with most variability occurring in the threefold proximal peaks, but the parvovirus genome in general presents highly conserved replication and structural genes across serotypes. All of the known serotypes can infect cells from multiple diverse tissue types. Tissue specificity is determined by the capsid serotype and pseudotyping of AAV vectors to alter their tropism range will likely be important to their use in therapy.

Adenoviruses (AdV) are medium-sized (90-100 nm), nonenveloped (without an outer lipid bilayer) viruses with an icosahedral nucleocapsid containing a double stranded DNA genome. They have a broad range of vertebrate hosts; in humans, more than 50 distinct adenoviral serotypes, belonging to seven species (A-G), have been found to cause a wide range of illnesses, from mild respiratory infections in young children (known as the common cold) to life-threatening multi-organ disease in people with a weakened immune system.

Methods of preparing recombinant AAV and AdV and packaging them into suitable host cells are known in the art. For AAV, viral production cells can include at least the minimum components required to generate AAV particles, where production of an AAV DNase resistant genome containing particles involves packaging an expression cassette into AAV capsids. The minimum required components include, for instance, an expression cassette to be packaged into the AAV capsids, AAV cap, and AAV rep or functional fragments thereof, and helper functions.

Suitable cells and cell lines have been described for use in production of AAV and AdV. The cells themselves may be selected from any biological organism, including prokaryotic (e.g., bacterial) cells and eukaryotic cells including insect cells, yeast cells and mammalian cells. Particularly desirable host cells are selected from among any mammalian species, including, without limitation, A549, WEHI, 3T3, 10T1/2, BHK, MDCK, COS 1, COS 7, BSC 1, BSC 40, BMT 10, VERO, WI38, HeLa, a HEK 293 cell, Saos, C2C12, L cells, HT1080, HepG2 and primary fibroblast, hepatocyte and myoblast cells derived from mammals including human, monkey, mouse, rat, rabbit, and hamster.

Generally, the expression cassette is composed of, at a minimum, a 5' AAV inverted terminal repeat (ITR), a nucleic acid sequence encoding a desirable therapeutic, immunogen, or antigen operably linked to regulatory sequences which direct expression thereof, and a 3' AAV ITR. In one embodiment, the 5' and/or 3' ITRs of AAV serotype 2 are used. However, 5' and 3' ITRs from other suitable sources may be selected. It is this expression cassette that is packaged into capsid proteins to form an AAV virion (particle).

In addition to the expression cassette, the cells contain the sequences which drive expression of AAV capsids in the cells (cap sequences) and rep sequences of the same source as the source of the AAV ITRs found in the expression cassette, or a cross-complementing source. The AAV cap and rep sequences may be independently selected from different AAV parental sequences and be introduced into the host cell in a suitable manner known to one in the art. While the full-length rep gene may be utilized, it has been found that smaller fragments thereof, i.e., the rep78/68 and the rep52/40 are sufficient to permit replication and packaging of the AAV.

The cells also require helper functions in order to package the AAV of the invention. Optionally, these helper functions may be supplied by a herpesvirus. In another embodiment, the necessary helper functions are each provided from a human or non-human primate adenovirus source, such as are available from a variety of sources, including the American Type Culture Collection (ATCC), Manassas, Va. (US).

The present disclosure also provides, in certain embodiments, compositions and methods for using the purified viruses as a therapeutic or vaccine agent.

EXAMPLES

The following examples are included to demonstrate specific embodiments of the disclosure. It should be appreciated by those of skills in the art that the techniques disclosed in the examples which follow represent techniques to function well in the practice of the disclosure, and thus can be considered to constitute specific modes for its practice. However, those of skills in the art should, in light of the present disclosure, appreciate that many changes can be made in the specific embodiments which are disclosed and still obtain a like or similar result without departing from the spirit and scope of the disclosure.

Example 1: Lysis, Extraction and Purification of Adeno-Associated Virus and Adenovirus from Host Cells This example tests a process for lysing, extracting and purifying AAV and AdV viral particles from their packaged cells (host cells). The example demonstrates that this process achieves higher recovery and purity of viral particles than conventional methods. In addition, this process is easy to implement and can be scaled up readily.

Methods and Materials

Dulbecco's Modified Eagle Medium (DMEM), Fetal Bovine Serum (FBS) and cell culture dishes were purchased from Fisher Scientific. 6-well and 12-well cell culture plates were purchased from Santa Cruz Biotechnology. Plasmid DNA Maxiprep kit was purchased from Qiagen. Lipofectamine 2000 Transfection Reagent was purchased from Life Technologies. DNase I, Maxima Sybr Green qPCR Master Mix (2×), Pierce BCA Protein Assay kit, SDS-PAGE minigels, Amicon Ultra-4 Centrifugal Filter and all chemicals were purchased from Fisher Scientific. Silica-based chromatography columns were purchased from Agilent Technologies, Inc. and Bonna-Agela Technologies Inc.

Cell Culture

HEK293 cells were grown in Dulbecco's Modified Eagle Medium (DMEM) containing 10% Fetal Bovine Serum (FBS) in a 37° C. incubator with 5% $CO_2$ and subcultured every 3-5 days. Cells were split 1:2 in 15-cm dishes for transfection for AAV packaging or for infection for AdV amplification. Cells were split onto 6-well or 12-well cell culture plates from infection testing.

AAV Packaging

Figure 3:
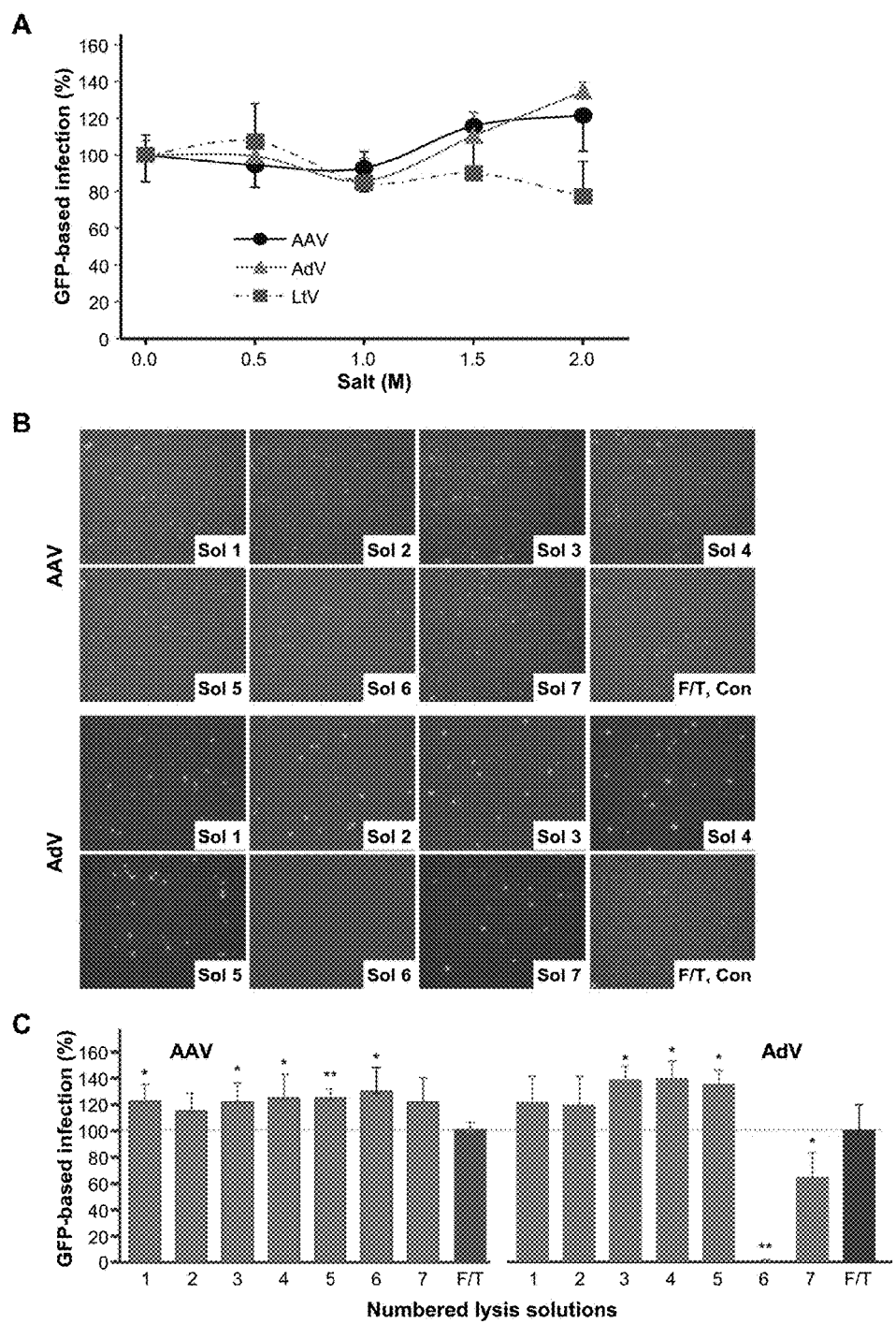
FIG. 3 with panels A-C shows that AAV and AdV viruses exhibit high tolerance to a range of high concentrations of salt that enables successful application of salting precipitation in purification of these viral particles. (A) AAV or AdV viruses were prepared as described in FIG. 1 and mixed with an equal volume of different concentrations of NaCl solutions as indicated. LtV virus was prepared and used for comparison in parallel. After 2 hours at room temperature, viral mixtures were used for infection as described in FIG. 1. The scatter chart is expressed as mean percentage±SD of GFP cell numbers, n=4. (B, C) AAV- or AdV-packaged cells were lysed using 7 alkaline lysis solutions as described in FIG. 2 and a salt solution of 3 M NaAc, pH 5.5 was added to each lysate for salting precipitation. After mixed, precipitates occurred and were removed by centrifugation. Supernatants were saved for infection as described in FIG. 1. Images shown are representatives of photos (B) and histograms are expressed as mean percentage±SD of GFP cell numbers (C). *, p<0.05; **, p<0.01, compared to that of freeze/thaw viruses (control), n=4.

HEK293 cells were split onto 15-cm dishes and transfected on the $2^{nd}$ day using Lipofectamine 2000 Transfection Reagent or calcium phosphate precipitation method. Plasmid DNA used for AAV packaging included GFP-recombinant AAV viral vector and AAV packaging plasmids. After overnight incubation, the medium was replaced with fresh growth medium and the transfected cells were incubated for additional two days before collecting cells by centrifugation at 2000 rpm for 5 minutes. The AAV-packaged cells were used for viral extraction immediately or stored at −80° C. until use. The medium was saved for PEG precipitation of viral particles within it. PEG precipitation was conducted using 6-8% PEG8000 and 1-hour incubation at 4° C., followed by centrifugation at 10,000 rpm for 10 minutes. The PEG precipitates were suspended in PBS by vortexing and pipetting followed by clarifying at 5000×g for 5 minutes. The viral suspensions were used in pH, detergent and salt testing as shown in FIG. 1 and FIG. 3 panel A.

AdV Generation

HEK293 cells were split onto a T75 flask and transfected with a GFP-recombinant adenoviral plasmid plus Lipofectamine 2000. The medium was replaced with fresh growth medium 24 hours post transfection. Cells were incubated for a week before harvesting cells. Cells were suspended in PBS and extracted by freeze/thaw 3 times, followed by clarifying at 5000×g for 5 minutes. One third of supernatant was used for infection of a T175 of HEK293 cells for further viral production and the rest was stored as primary stock. The infected cells were collected after a week of incubation and the viral particles were extracted by freeze/thaw 3 times as stock at −80° C. until use for viral production. For testing assays, 15-cm dishes of HEK293 cells were incubated for 3-5 days after infection with AdV virus until >90% cells were cytopathic. Cells were then collected by centrifugation at 2000 rpm for 5 minutes. Cell pellets were used for viral extraction immediately or stored at −80° C. until use. The medium was saved for PEG precipitation of viral particles within it. PEG precipitation was conducted as the same as described above for AAV and viral suspensions were used in pH, detergent and salt testing.

Condition Testing

AAV and AdV viral solutions were mixed with an equal volume of pH buffered solutions, detergent solutions or salt solutions as indicated in figures and incubated at room temperature for 2 hours before used for infection in HEK293 cells. Infectivity visualized by GFP was investigated to estimate the viral activity. Determination of the ranges of pH value and amounts of detergents suitable for AAV and AdV viruses to maintain their activities is aimed to design cell lysis solutions to easily release the viral particles from their packaging cells. Determination of the viral suitability to a range of salt solutions is expected to learn the possibility to employ salting precipitation in the viral purification procedures.

Viral Purification

Lysis of host cells is an important step that enabled rapid lysis of the viral host cells and complete release of the viral particles. Based on the results from condition testing that AAV and AdV viruses were able to maintain their activities in a wide range of pH values and certain amounts of detergents such as sodium dodecyl sulfate (SDS) and sodium deoxycholate (DOC), a serial of lysis solutions were designed, including various acidic solutions and alkaline solutions without or with addition of detergents as shown in Table 2 and 3. After the discovery that alkaline solutions with addition of detergents such as DOC or DOC plus SDS achieved effective lysis of AAV- and AdV-packaged cells, various alkaline lysis solutions were further prepared and tested as shown in Table 4 and 5. Suitable detergents used here could also include deoxycholate, octyl thioglucoside, octyl glucoside, dodecyl maltoside, octyl thioglucoside, octyl glucoside, alkyl Sulfates, Polysorbate 20 (Tween-20), Tergitol-type NP-40 and their combinations. In process, AAV- or AdV-packaged cells were collected by centrifugation at 2000 rpm for 5 minutes and then lysed in the above lysis solutions. Cells were lysed with radioimmunoprecipitation assay (RIPA) buffer [25 mM Tris-Cl, pH 7-8, 150 mM NaCl, 0.1% SDS, 0.5% sodium deoxycholate (DOC), 1% NP-40 and cocktail protease inhibitors] as total protein control or extracted using 3 cycles of freeze in −80° C. and thaw in a 37° C. water bath as comparative control.

As an extraction step, we first tested the possibility to use salting precipitation to remove the host cell proteins but retain the viral particles in supernatants. After testing the tolerance of AAV and AdV viruses to salt as described above in which we found that both of the viruses display wide suitability to high salt, we prepared serials of various salt solutions (Table 6) for test of salting precipitation in the viral extraction following cell lysis. Salt solutions were added to cell lysates and were mixed quickly. After salting precipitation occurred, the mixed solutions were clarified by high-speed centrifugation and removed the precipitates. Supernatants were used for infection in HEK293 cells to validate viral particles remaining in solution. It was demonstrated that salting precipitation process removed the majority of impurities of host cell proteins and efficiently retained the viral particles in solution, the extracted viral solutions considerably cleaner that could be further processed with PEG fractionation or directly used for further purification by column chromatography.

PEG fractionation was then tested to desalt, enrich and further purify the extracted viral solutions following salting process. Various sizes of PEG with average molecular weights from 3000 to 10000 were tested by making stock solutions and adding different amounts to the viral solutions. After mixing, the mixtures were incubated on ice for 0.5-2 hours and then centrifuged at a high speed for 15 minutes to precipitate the viral particles. The viral particles were resuspended in PBS for infection to validate the viruses or in an appropriate buffer for further purification by column chromatography. It was found that PEG fractionation led to high-purity viral solutions that could be suitable in use for many research purposes.

The next step was column chromatography purification of the AAV and AdV particles, followed by concentration of the viral solutions with centrifugal filters, in order to yield high-titer, ultrapure viral solutions. AAV or AdV viral particles, either the extracted viral solutions from salting process or the resuspended viral solutions from PEG fractionation, were applied onto the chromatography columns that were silica-based chromatography, resin chromatography or ion exchange chromatography columns. Serials of viral suspension buffers, column washing buffers and elution buffers were prepared and optimized for different chromatography columns. The viral eluents were concentrated using Amicon Centrifugal Filters or other centrifugal filters.

Infectivity Assay

Infection in HEK293 cells was performed as major means of investigation of viral activities in developing the present techniques for purification of AAV and AdV particles. Cells were split in 12-well or 6-well plates with 80-90% confluence in DMEM containing 5% FBS per well one day before use for infection. Amount of viral solutions were added to each well according to viral concentrations, ionic strength and pH value of the viral solution, ranged about 1-10 µl per well or diluted before used for infection. Since all viruses used are GFP-contained, the infectivity was investigated by viewing GFP cells that were photographed and counted under a fluorescence microscope. Photographs were taken under a 4× lens and GFP cells were counted in fields of a 10× lens. AdV infectivity was investigated in 2-3 days after infection while AAV infectivity was investigated in 3-5 days. It was important that GFP cells after infection were countable in fields of a 10x lens. If numbers of GFP cells were too high or too low to count, infection was repeated with adjusted amounts of viral solutions or with new viral solutions from repeated experiments.

qPCR Titration

AAV and AdV viral solutions after chromatography column purification were titrated using quantitative real-time PCR (qPCR). The viral solutions were first treated with DNase I in 10 µl reaction mixture containing 5 units of DNase I and then titrated by means of qPCR in 25 µl reaction mixture containing 2× Sybr Green qPCR Master Mix and one pair of primers as listed in Table 1 using a standard qPCR cycling paradigm. Serials of 10-fold dilutions of viral vectors were used as standards in the qPCR titration. Titers of viral solutions were calculated as viral genomic copies per milliliter (ml) using the standard curves.

TABLE 1

Primers were used in qPCR for AAV viral titration.

| Target | ID | Sequences (SEQ ID NO: _) | Amplicon | Titration virus |
|---|---|---|---|---|
| GFP | Fw_GFP: | 5'-TCTGCACCACCGGCAAGCTGC-3' (SEQ ID NO: 1) | 76 bp | AAV or AdV |
|  | Rv_GFP: | 5'-GAGAAGCACTGCACGCCGTAG-3' (SEQ ID NO: 2) |  |  |
| hGH_PA | Fw_pA: | 5'-GGTCTCCAACTCCTAATCTCAG-3' (SEQ ID NO: 3) | 102 bp | AAV |
|  | Rv_pA: | 5'-AAAATCAGAAGGACAGGGAAGG-3' (SEQ ID NO: 4) |  |  |
| CMV | Fw_CMV: | 5'-TTCCTACTTGGCAGTACATCTACG-3' (SEQ ID NO: 5) | 128 bp | AdV |
|  | Rv_CMV: | 5'-GTCAATGGGGTGGAGACTTGG-3' (SEQ ID NO: 6) |  |  |

BCA Assay

Protein amounts contained in viral solutions were determined using bicinchoninic acid assay (BCA assay) following the BCA Protein Assay Kit's protocol. Briefly, the assays were conducted by adding 25 µl sample solutions and 200 µl BCA solution (mixed A and B, 50:1) per well in 96-well plates. The plates were incubated at 37° C. for 30 minutes, followed by reading at 562 nm using a plate reader. Bovine serum albumin (BSA) was used to make a standard curve with serial dilutions from a stock of 10 mg/ml. To lower influence from higher salt concentration in solutions after salting precipitation, two strategies were used: (1) The high salt samples were diluted 5 folds in H2O, so that 5 µl sample plus 20 µl H2O was added per well for BCA assay; (2) A similar salt solution (salt mix) was prepared and 5 µl of the salt mix was added to each well of those of low salt samples including standard dilutions to reduce the influence of high salt in BCA assay.

SDS-PAGE Electrophoresis

Protein amounts contained in viral solutions were visualized by means of SDS-polyacrylamide gel electrophoresis (SDS-PAGE) electrophoresis. Viral solutions from alkaline lysis/salting precipitation were diluted 4 fold with $H_2O$ and then mixed with 5×SDS sample buffer. Sample solutions from freeze/thaw and RIPA lysis were mixed with 5×SDS sample buffer and then diluted with 1×SDS sample buffer. All samples were portioned in the same volume based on original cell suspensions and same volume of each sample was loaded onto 10% SDS gels. Gels were run at 140 Voltages for about 1 hour until the dye bromophenol blue reached at the gel's bottom. After electrophoresis, gels were fixed in a fixing solution containing 50% (v/v) methanol in water with 10% (v/v) acetic acid before staining overnight in a Coomassie Blue Staining solution containing 50% (v/v) methanol in water with 10% (v/v) acetic acid and 0.25% (w/v) Coomassie Blue R-250. Destaining was performed in a destaining solution containing 50% methanol and 10% acetic acid. After completely destaining, gels were kept in 5% (v/v) acetic acid. Gels were scanned into image files using a scanner, of which density of gels were quantified using NIH Image J.

Results

Adeno-Associated Virus and Adenovirus Maintain their Infectivity in a Wide Range of pH Values from about 3.6 to about 11.5.

This example first tested the suitability of AAV and AdV to a wide range of pH values from about 3.6 to about 11.5 in order to determine pH values for development of desirable cell lysis solutions. Viral solutions were incubated with the indicated pH solutions for 2 hours at room temperature before used for infection in HEK293 cells. Through investigation of their GFP expression, we found that AAV maintained its infectivity at all tested pH values from pH 3.6 to pH 11.5 and AdV was stable to maintain its infectivity at the pH values from pH3.6 to pH10.5 but unstable over pH 11.0 (FIG. 1 panels A and B). In contrast, LtV was used for comparison, which has a narrow range of pH values from pH 6.0 to pH 9.5 to maintain its infectivity (FIG. 1 panels A and B). These results, therefore, suggest determining the desired pH values of cell lysis solutions from pH 3.6 to pH 11.5 for AAV and from pH 3.6 to pH 10.5 for AdV that mostly conduce to lysis of cells and do not obviously affect the viral activity.

Adeno-Associated Virus and Adenovirus Maintain their Infectivity in a Range of Amounts of Sodium Deoxycholate from about 0.1% to about 1.0%, but are Sensitive to Sodium Dodecyl Sulfate.

To test the possibility to use detergents in cell lysis solutions for lysis of AAV- and/or AdV-packaging cells, we determined the tolerance of these viruses to detergents including sodium dodecyl sulfate (SDS), Triton X-100 and sodium deoxycholate (DOC) that are commonly used for cell lysis. Viral solutions were incubated with the indicated detergents for 2 hours before used for infection. HEK293 cells are very sensitive to Triton X-100 but not to SDS and DOC in amounts used in the testing, implicating that Triton X-100 may be toxic to the viruses. SDS treatment was stringent to both viruses, which shows that AdV is more sensitive, even 0.1% SDS abolished all viral infectivity but AAV infectivity was also dramatically decreased with increased SDS concentrations, 30% down at 0.1% SDS and 50% down at 0.5% SDS (FIG. 1 panels C and D). In contrast, both viruses maintain high infectivity in a range of DOC amounts from 0.05% to 1.0% tested (FIG. 1 panels C and D). It is therefore suggested from these results that DOC, but neither SDS nor Triton X-100, is the best candidate of detergent for cell lysis solutions because of it's compatibility with both AAV and AdV viruses.

Alkaline Solutions, but not Acidic Solutions, Partially Lyse Viral Host Cells

According to suitable pH values determined above, we prepared several acidic solutions and alkaline solutions (Table 2) to test whether HEK293 cells—the viral packaging cells could be lysed under acidic and/or alkaline conditions. Cells were collected and resuspended in these solutions respectively. After mixing, we found that cells-suspended alkaline solutions were much clearer than cells-suspended acidic solutions, the former with a little of pellets out while the later with much more pellets out after centrifugation at 5000 rpm for 2 minutes (Table 2). It is obviously indicated that alkaline solutions with pH9.0-11.5 partially, but not completely, lyse the viral host cells while acidic solutions with pH3.6-5.0 did not lyse the cells. Thus, it is concluded that these alkaline solutions, although better than acidic solutions, are not capable to completely lyse the viral host cells.

TABLE 2

HEK293 cells are partially lysed in alkaline, but not acidic, solutions.

| Lysis solutions | | | | Cell lysis | |
| --- | --- | --- | --- | --- | --- |
| Type | Component | pH | Visible | Spin (5000 rpm, 2 min) | |
| Acidic | HCl, 0.1-0.5N | ~1 | Not lysed | Pellet out | |
| | NaAc, 0.1-0.5M | 3.6-5.0 | Not lysed | Pellet out | |
| Alkaline | NaOH, 0.1-0.5N | ~13 | Lysed | No pellet | |
| | Glycine/Na, 0.1-0.5M | 9.0-11.5 | Not fully Lysed | Small pellet | |

Detergents Enable Alkaline Solutions to Efficiently Lyse AAV and AdV Packaging Cells.

As determined above, AAV and AdV were sensitive to SDS but compatible to DOC (FIG. 1 panels C and D). Therefore, we tested whether DOC or DOC plus SDS improves cell lysis by adding 0.1%-1.0% DOC with or without 0.01%-0.2% SDS to the above alkaline solutions and found that addition of the detergents led to complete lysis of cells in the pH range of pH 9.6-11.5 tested (Table 3). Other detergents, including deoxycholate, octyl thioglucoside, octyl glucoside, dodecyl maltoside, octyl thioglucoside, octyl glucoside, alkyl Sulfates, Polysorbate 20 (Tween-20), Tergitol-type NP-40 and their combinations, may be also suitable to conduce to cell lysis. Therefore desirable alkaline lysis solutions are suggested that contain reagents or compounds with buffering capability of pH9.0-11.5 and appropriate amounts of detergents such as DOC and SDS.

TABLE 3

Sodium deoxycholate enables alkaline solutions to completely lyse HEK293 cells.

| Alkaline solutions | | | | Cell lysis | | |
|---|---|---|---|---|---|---|
| Alkaline solutions | pH | DOC | SDS | Visible | Spin 1 | Spin 2 |
| NaOH, 0.1-0.5N | ~13 | 0.1%-1.0% | No | Lysed | No pellet (5K rpm 2 min) | No pellet (10K rpm 2 min) |
|  |  | 0.1%-1.0% | 0.01%-0.5% | Lysed |  |  |
| Glycine/Na, 0.1-0.5M | 90-11.5 | 0.1%-1.0% | No | Lysed | No pellet (5K rpm 2 min) | No pellet (10K rpm 2 min) |
|  |  | 0.1%-1.0% | 0.01%-0.5% | Lysed |  |  |

Multiple Alkaline Solutions Effectively Lyse HEK293 Cells with Addition of Detergents.

Figure 2:
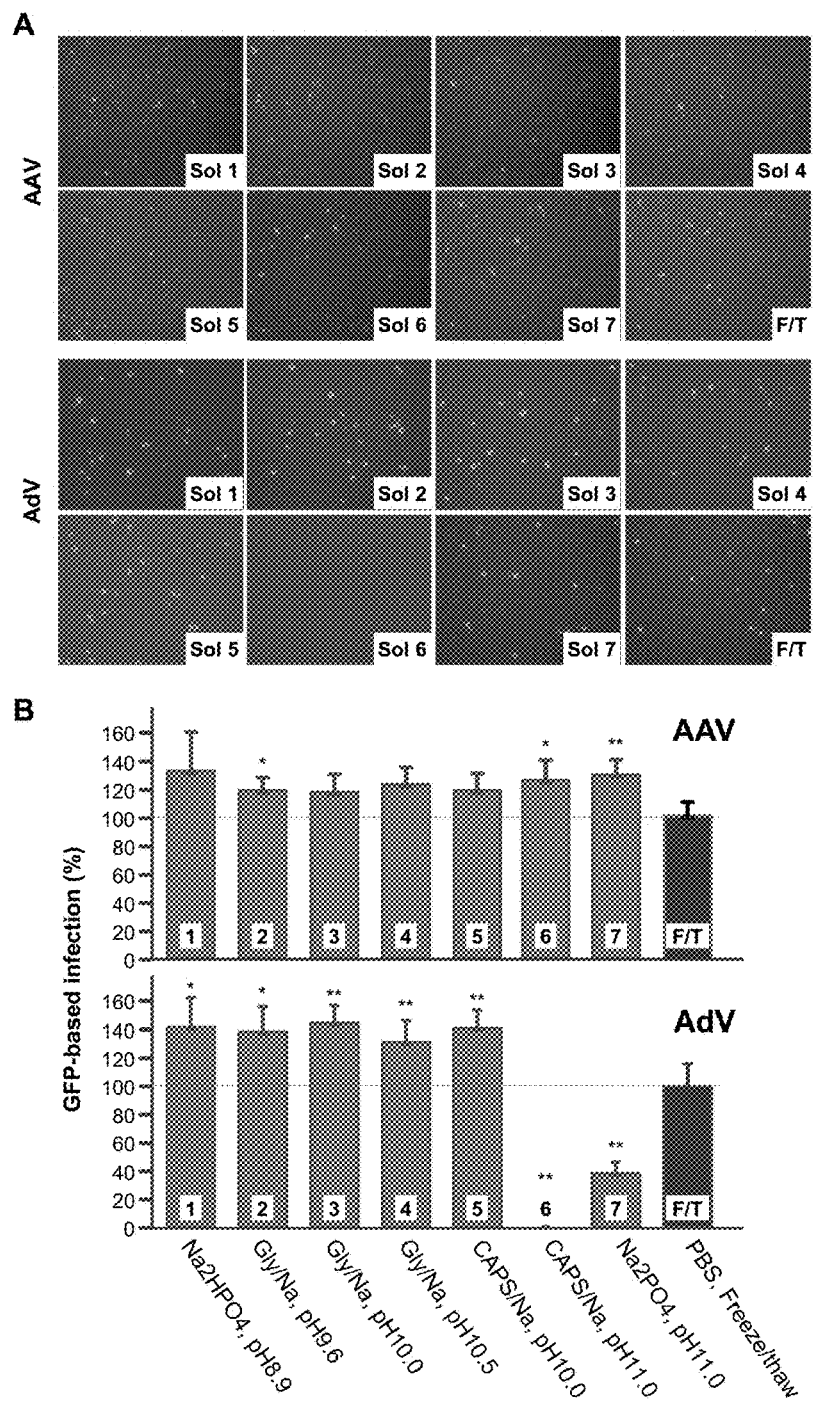
FIG. 2 with panels A-B shows that AAV and AdV particles are completely released after lysis of their packaged cells using various alkaline solutions with an appropriate amount of detergent. Seven alkaline lysis solutions were prepared according to the tolerance of AAV and AdV to pH values and detergents demonstrated in FIG. 1 and used for lysis of AAV- or AdV-packaged HEK293 cells as indicated. The lysates were used for infection in HEK293 cells as described in FIG. 1 and the viral extracts from AAV- or AdV-packaged cells using freeze/thaw (F/T) 3 times were used as comparative control. (A) Images of GFP cells shown are representatives of photos and (B) histograms are expressed as mean percentage±SD of GFP cell numbers. *, p<0.05; **, p<0.01, compared to that of freeze/thaw extracted viruses (control), n=4.

We further investigated cell lysis with different kinds of alkaline solutions containing detergent DOC as example as listed in Table 4 and found all these kinds of alkaline solutions are efficient in lysis of HEK293 cells. Next, we chose 7 kinds of alkaline solutions as listed in Table 5 to lyse AAV- and AdV-packaged cells and investigated viral infectivity after lysis. It is known that freeze/thaw is most commonly used to extract AAV and AdV particles, so we extracted AAV or AdV particles from their packaged cells using freeze/thaw three times in parallel as comparative control. Viral infectivity was determined by investigation of GFP-expressed cells that were photographed (FIG. 2 panel A) and counted (FIG. 2 panel B). We found that these alkaline solutions are all effective in lysing the host cells and release both AAV and AdV viral particles that displayed higher infectivity than those extracted by freeze/thaw (FIG. 2 panels A and B). Consistent to the results from pH testing above, AdV infectivity was much decreased in the alkaline lysis solutions with pH11.0 (FIG. 2 panels A and B). It is therefore concluded that alkaline solutions plus appropriate amounts of detergents such as DOC are sufficient to lyse AAV- and AdV-packaged cells and completely release the viral particles, the pH9.0 to 11.5 for AAV and the pH9.0 to 10.5 for AAV. This new cell lysis method can overcome the shortages of freeze/thaw method including time-consuming and viral activity-decreasing.

TABLE 4

Multiple alkaline solutions with DOC effectively lyse HEK293 cells.

| Alkaline lysis solutions | | | |
|---|---|---|---|
| Chemicals | Concentration | pH | Cell lysis |
| $Na_2HPO_4$ | 0.1-0.5M | ~9 | Good |
| $K_2HPO_4$ | 0.1-0.5M | ~9 | Good |
| Glycine/NaOH | 0.1-0.5M | 9.5-10.5 | Good |
| Tris base | 0.1-0.5M | ~10 | Good |
| CAPS/NaOH | 0.1-0.5M | 10.0-11.5 | Good |
| $Na_2CO_3$/NaOH | 0.1-0.5M | 10.5-11.0 | Good |
| $Na_2HPO_4$/NaOH | 0.1-0.5M | 10.5-11.0 | Good |

TABLE 5

Alkaline solutions are used for lysis of virus-packaged cells.

| Alkaline lysis solutions | | | Viral activity | |
|---|---|---|---|---|
| No. | Chemicals | pH | AAV | AdV |
| 1 | $Na_2HPO_4$ | 8.9 | Good | Good |
| 2 | Glycine/NaOH | 9.6 | Good | Good |
| 3 |  | 10.0 | Good | Good |
| 4 |  | 10.5 | Good | Good |
| 5 | CAPS/NaOH | 10.0 | Good | Good |
| 6 |  | 11.0 | Good | No |
| 7 | $Na_2HPO_4$/NaOH | 11.0 | Good | No |

Salting Precipitation is Suitable to Precipitate Protein Impurities and Retain AAV and AdV Viral Particles in Solutions.

Massive host cell proteins exist in viral solutions as their packaged cells are lysed. How to remove these protein impurities is the major concern in these viral purifications. It is known that salting precipitation is a potent technique commonly used in protein chemistry. To test the possibility using salting precipitation to remove proteins in viral solutions, we investigated the tolerance of AAV and AdV to high salt solutions and found that both AAV and AdV maintain highly consistent infectivity after incubation with solutions of salt up to 2.0 M NaCl, while LtV, in contrast, shows less tolerance to high salt solutions (FIG. 3, panels A). These results implicate the possibility that salting precipitation could be used to remove protein impurities in these viral solutions.

In test of salting precipitation, we lysed AAV- and AdV-packaged cells in the 7 kinds of alkaline lysis solutions as listed in Table 5, to these cell lysates 0.5-3 M NaAc, pH 5.5 was added and mixed quickly. As expected, large precipitation occurred. The precipitates were removed by centrifugation and the supernatants were saved for infection. Results of viral infectivity show that both kinds of the viral particles perfectly remain in the supernatants after salting precipitation (FIG. 3 panels B and C). Importantly, we found that the new method using alkaline lysis/salting precipitation produced AAV and AdV particles 20-40% higher than those extracted by freeze/thaw (FIG. 3 panels B and C), suggesting that alkaline lysis is more efficient than freeze/thaw to release AAV and AdV viral particles from their host cells.

Salting Precipitation Removes the Majority of Host Cell Proteins from AAV and AdV Solutions.

Figure 4:
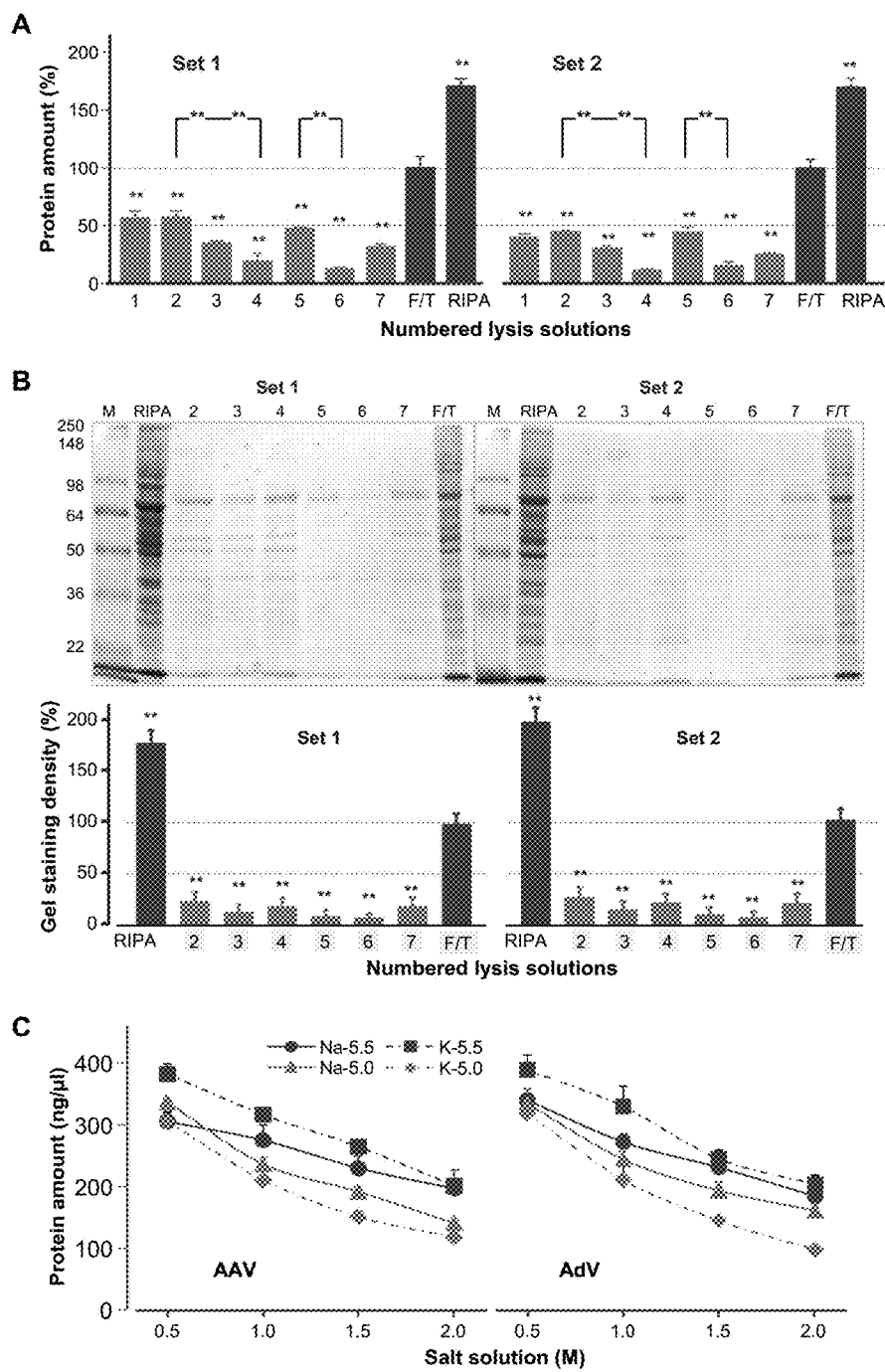
FIG. 4 with panels A-C shows that salting precipitation removes the majority of protein impurities from alkaline lysates of AAV- and AdV-packaged cells in a salt dose-dependent manner. (A, B) Normal HEK293 cells (Set 1) or AAV-packaged HEK293 cells (Set2) were lysed using 7 alkaline lysis solutions as described in FIG. 2, followed by salting precipitation process as described in FIG. 3. The extracted samples were used for BCA protein assay (A) or SDS polyacrylamide gel electrophoresis (PAGE) analysis (B). In parallel, extracts by freeze/thaw (F/T) 3 times were prepared as comparative control and cell lysates using RIPA buffer was prepared as total protein control. Results from BCA assay are expressed as mean percentage±SD of protein amount, **p<0.01, compared to that of freeze/thaw viruses (control), n=6 (A). Results from PAGE analyses are shown as images that are representatives of PAGE gels and expressed as mean percentage±SD of staining density, *, p<0.05; **, p<0.01, compared to that of freeze/thaw viruses (control), n=3 (B). (C) AAV viruses or AdV viruses were packaged and lysed with a solution of Glycine/Na, pH 10.0 and processed for salting precipitation using different amounts of NaAc (pH5.0 or 5.5) or KAc (pH5.0 or 5.5) as indicated. Extracted viral solutions were used for BCA assay. Scatter charts are expressed as mean percentage±SD of as protein amount, n=5.

To determine the effectivity of salting precipitation, we prepared two sets of samples: Set 1 used normal HEK293 cells and Set 2 used AAV-packaged HEK293 cells, and lysed these cells with alkaline lysis solutions followed by salting precipitation. After centrifugation to remove out precipitates, protein concentrations in the supernatants were measured by BCA assay (FIG. 4 panel A) and SDS-PAGE electrophoresis (FIG. 4 panel B). Both results consistently display that the majority of protein impurities in all the cell lysates was removed by salting out in comparison with whole cell lysate (RIPA buffer lysed) and extract by freeze/thaw (FIG. 4 panels A and B). Furthermore, a trend is observed that higher pH of alkaline lysis solutions led to more proteins removal (FIG. 4 panels A and B).

Investigation of salting-out effectiveness of various salt solutions discovered a variety of salts are suitable for salting precipitation to precipitate impurities out and retain the viral particles in solutions except ammonium salts that inhibit the infectivity of both AAV and AdV viruses (Table 6). Besides, salt doses and pH values of salt solutions were further demonstrated that protein removal by salting precipitation is salt dose dependent and can be shifted up with lower pH (FIG. 4 panel C).

TABLE 6

Various salt solutions and their effectiveness in salting precipitation

| Salt solution | | | Effectiveness | |
| --- | --- | --- | --- | --- |
| Chemicals | Concentration | pH | Protein removal | Viral activity |
| NaH2PO4 | 1.0-4.0M | 4.0-6.0 | Good | Good |
| NaAc | 1.0-4.0M | 4.0-6.0 | Good | Good |
| KAc | 1.0-4.0M | 4.0-6.0 | Good | Good |
| NH4Ac | 1.0-6.0M | 4.0-6.0 | Good | Inhibited |
| NaCl | 1.0-4.0M | 4.0-6.0 | Good | Good |
| KCl | 1.0-4.0M | 4.0-6.0 | Good | Good |

Polyethylene Glycol Fractionation Desalts and Enriches AAV and AdV Particles

Figure 5:
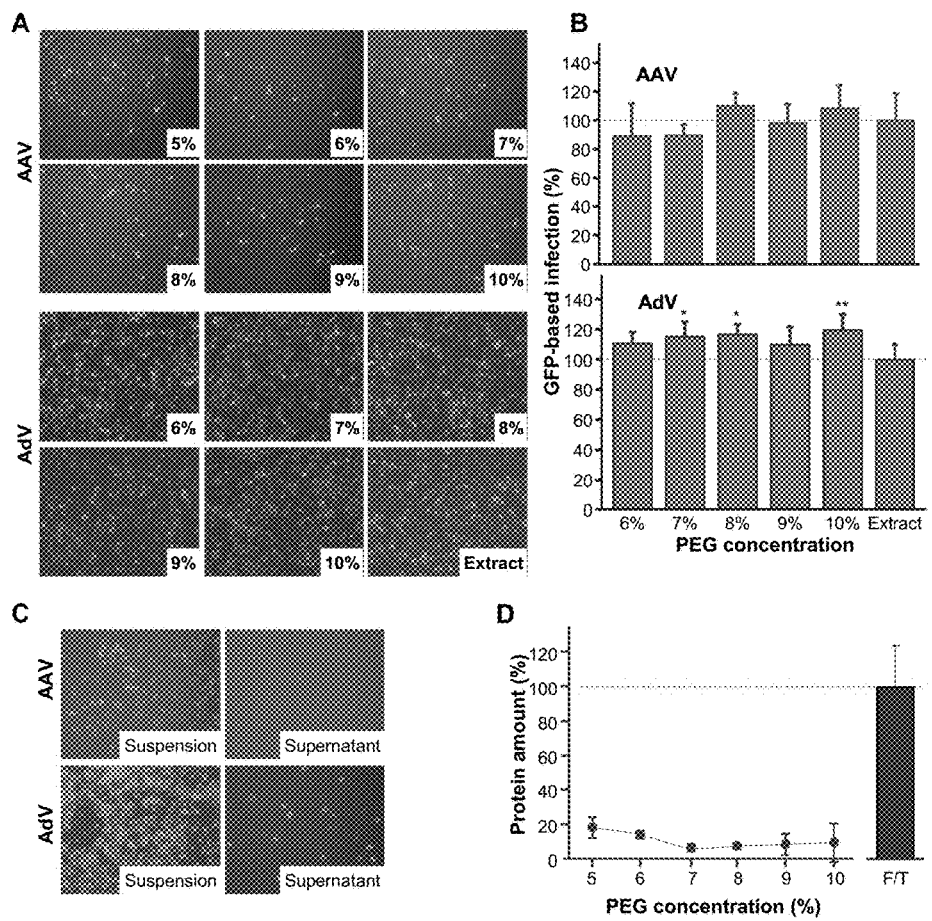
FIG. 5 with panels A-D shows that PEG efficiently fractionates viral particles into precipitates from extracted viral solutions after salting process resulting in viral particles desalted, enriched and further purified. AAV- or AdV-packaged cells were lysed with Glycine/Na, pH 10.0, followed by salting process as described in FIG. 3. The extracted viral solutions were mixed with different amounts of PEG8000 as indicated. Precipitates after PEG fractionation were suspended in PBS and used for infection or BCA assay. (A) Results from infection are shown as images that are representatives of photos. (B) Results from infection are shown as in histograms that are expressed as mean percentage±SD of GFP cell numbers. *, p<0.05; **, p<0.01, compared to that of freeze/thaw viruses (control), n=6. (C) Results from infection are shown as images that are representatives of photos, which demonstrate that PEG efficiently fractionates AAV and AdV particles into precipitates. (D) Results from BCA assay are shown in a scatter chart that are expressed as mean percentage±SD of protein amount, n=5.

The next step attempted to separate the viruses from the high salt solutions either using column chromatography as described below or through fractionation of viral particles into a fraction of solution or precipitate with organic solvents or a polymer such as polyethylene glycol (PEG). In test of desalting, viral particles of both AAV and AdV were found able to be fractionated in a two-phase system including Na—HPO4/PEG or K—PO4/PEG or precipitated by organic solvents such as acetone and isopropanol. These methods, however, lead to decrease the viral infectivity (data not shown). Use of various molecular sizes of PEG from PEG3000 to PEG 10000 showed effective fractionation of the two kinds of viruses from the high salt solutions into precipitates (data not shown). For example as shown in FIG. 5 panels A and B, various amounts of PEG8000 were able to precipitate both AAV and AdV viral particles that were resuspended in PBS. Results from infection show that PEG fractionation yielded an extremely high recovery of the two kinds of viruses (FIG. 5 panel C) and its selectivity for precipitation of the viral particles leading to further removal of contaminant proteins (FIG. 5 panel D). It is, therefore, concluded that PEG fractionation is an excellent step that desalts, enriches and further purifies the viral particles following alkaline lysis/salting precipitation processes. Importantly, the viral solutions of AAV or AdV resulted from PEG fractionation are high-quality viral preparations that can be used for many research purposes.

Various Kinds of Column Chromatography Yield Ultrapure Viral Particles of AAV and AdV.

Figure 6:
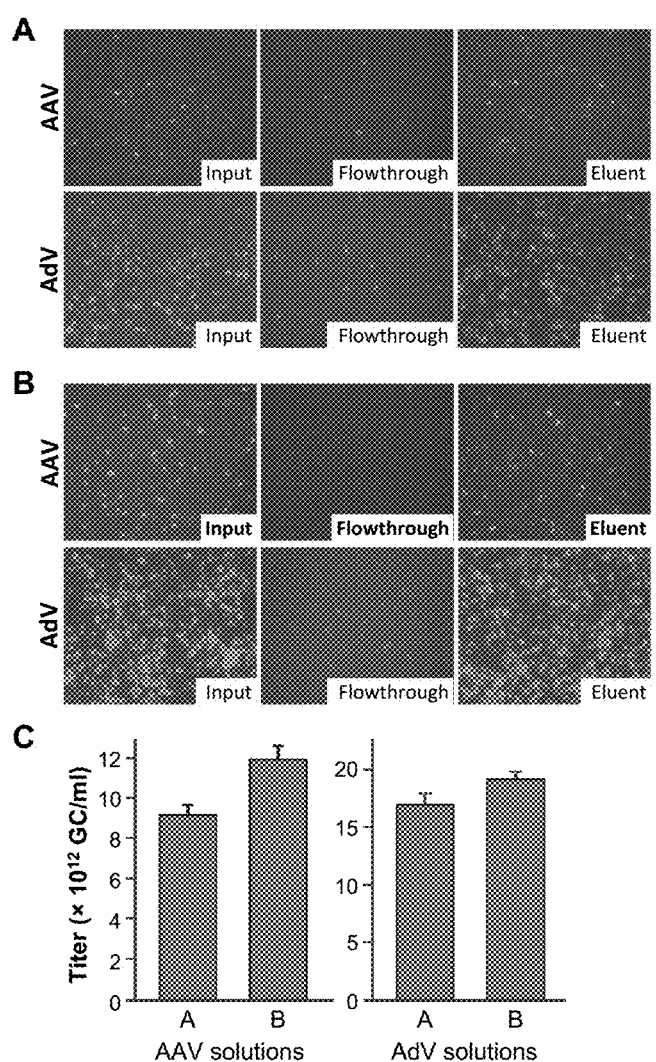
FIG. 6 with panels A-C shows that silica-based chromatography as example is capable to further purify AAV and AdV viral particles. (A) AAV particles or AdV particles were extracted using alkaline lysis/salting precipitation as described in FIG. 3 and the extracted viral solutions were further purified using silica-based chromatography columns. (B) AAV particles or AdV particles were PEG precipitated following alkaline lysis/salting precipitation processes, resuspended in an appropriate solution and applied to silica-based chromatography columns. (C) AAV or AdV solutions eluted from columns as described in panels A and B were concentrated using Amicon Centrifugal Filter (Ultrcel-100K). After concentration, the resulting viral solutions were titrated by means of qPCR. Titers of these viral solutions were calculated as shown in histograms that are expressed as mean±SD of viral genomic copies (GC) per ml, n=4.

Although the viral solutions resuspended from PEG fractionation are in high quality and suitable for research purposes, further efforts were made to increase the purity of the viral particles in order to meet the requirements in use for all research purposes and/or preclinical or clinical trials. A desired choice of technique is a kind of column chromatography that is an easy, efficient and scalable technique. In testing, we found that various kinds of column chromatography are able to further purify both AAV and AdV viral particles, including silica-based chromatography columns, resin and ion exchange chromatography columns (Data not shown). As example shown in FIG. 6, a kind of cation exchange columns were used to purify AAV or AdV particles from viral solutions extracted using alkaline lysis/salting precipitation as described in FIG. 3 (panel A) and silica-based chromatography columns were used to purify AAV or AdV particles from viral resuspensions of PEG precipitates as described in FIG. 5 (panel B). After concentration of the eluted viral solutions from these columns, the resulting viral solutions were titrated using qPCR, which show high titers about $10^{13}$ GC/ml of AAV or higher than $10^{13}$ GC/ml of AdV (FIG. 6 panel C).

Figure 7:
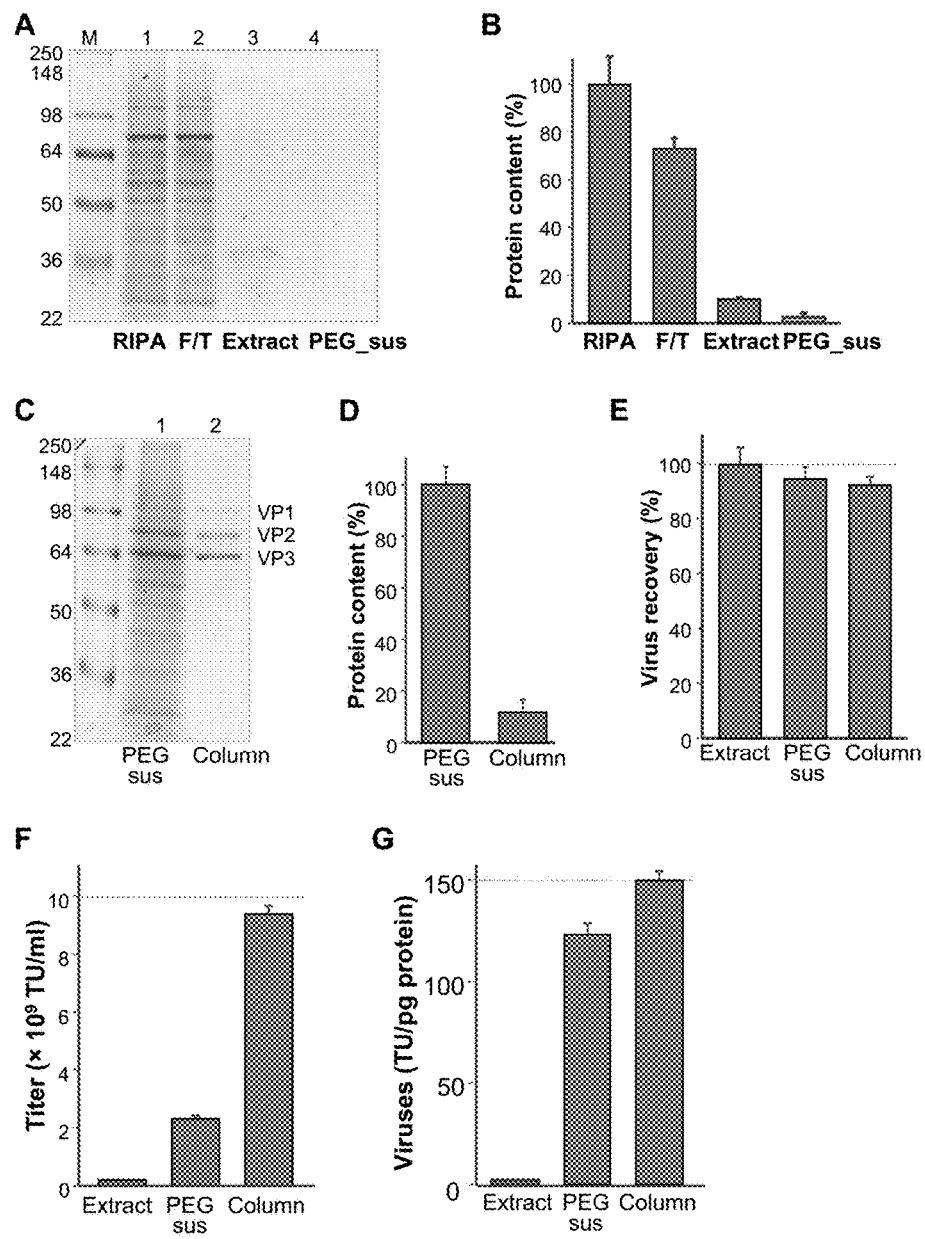
FIG. 7 with panels A-G shows that purification of AAV as example demonstrates that the present approach yields a high-titer, ultrapure viral solutions. AAV-packaged cells were lysed with RIPA buffer (RIPA) as total protein sample or by freeze/thaw (F/T) as comparative control or extracted using alkaline lysis/salting precipitation process (Extract) that was then PEG fractionated resulting in a suspension of PEG precipitate (PEG_sus) as described in FIG. 5. The viral suspension was applied onto a silica-based chromatography column and the eluent was concentrated using a centrifugal filter to yield the resulting solution (Column) as described in FIG. 6. These samples were analyzed by PAGE gel electrophoresis (A, C), BCA assay (B, D) or infection in HEK293 cells (E, F) as indicated. The purity of AAV viral solutions was calculated to express as viral transducing units (TU) per pg protein (G). (A-D) Results from PAGE gel analysis are shown as images that are representatives of gels (A, C) and results from BCA assay are shown as histograms that are expressed as mean percentage±SD of protein amount, n=5 (B, D). (E-G) Results from infection are shown as histograms that are expressed as mean percentage±SD of GFP cell numbers (E, n=6), as mean±SD of transducing units (F, n=6) or as mean±SD of viral particle numbers per pg protein (G, n=6).

The whole procedure we present here for purification of AAV and AdV viral particles include 3 continuous steps to remove protein impurities. After cell lysis using an alkaline lysis, salting precipitation processed using a high salt solution is the first step that removes the majority of host cell proteins, about 80-90% (FIG. 7 panels A and B). PEG fractionation is the following step that further removes contaminant proteins from the viral particles, about 70-80% (FIG. 7 panels A and B). Chromatography purification is the final step that removes remaining contaminant proteins and ensures ultrapurity of the viral solutions (FIG. 7 panels C and D) that can be concentrated using a centrifugal filter to yield a final high-titer viral solution (FIG. 7 panels E-G). The new procedures used for the two viral purifications are characterized ultrahigh purity (near 100% viral particles) (FIG. 7 panels C, D and G), high recovery (>90%) (FIG. 7 panel E) and high titer ($10^{10}$ TU/ml) (FIG. 7 panel F).

The Artistic Approach Exhibits Unparalleled Advantages in Production of High Purity AAV Solution.

Figure 8:
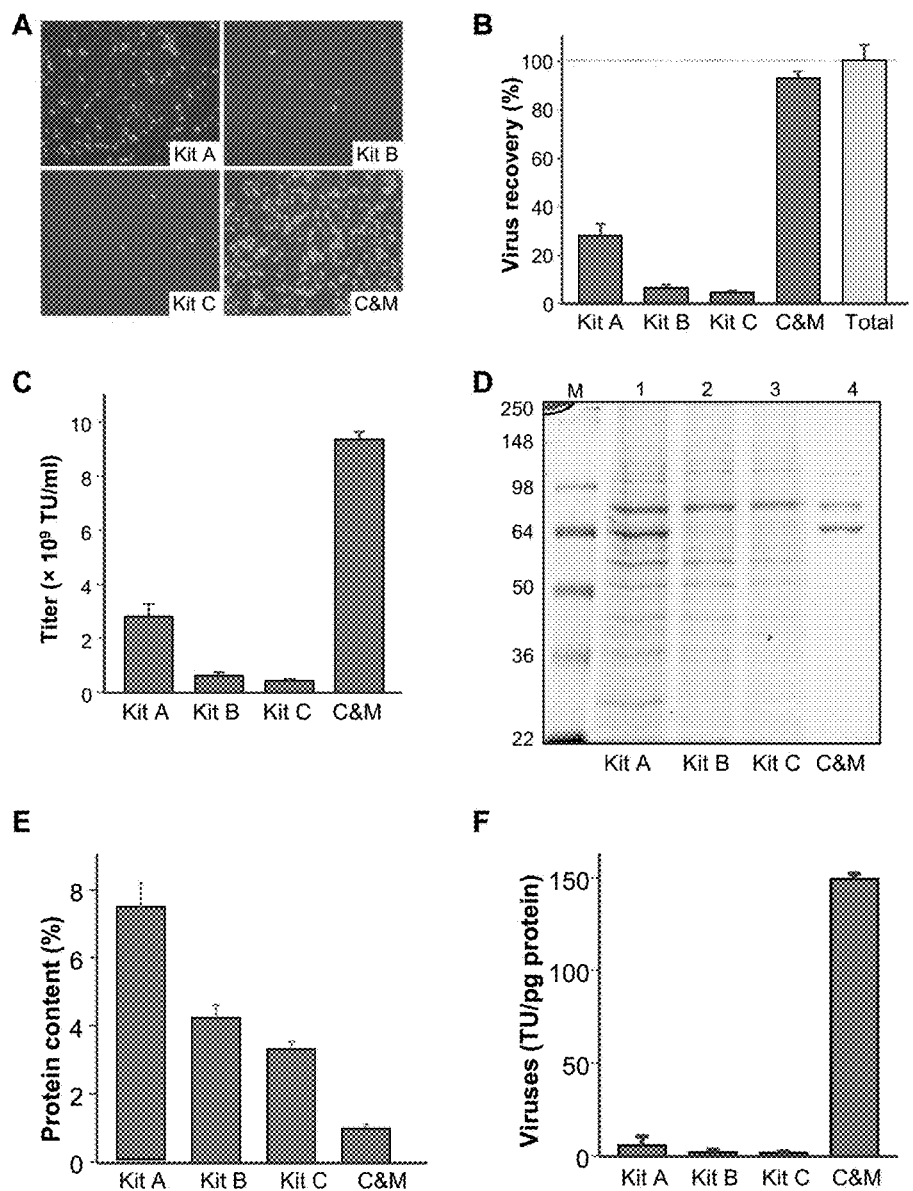
FIG. 8 with panels A-F shows that the present approach with the characteristics to yields high recovery and purity of AAV viral solution as example is unparalleled in the commercial market. AAV packaged cells were collected and equally divided into 4 portions that were used for AAV purification by means of 4 different procedures, 3 commercial kits (marked as Kit A, Kit B and Kit C) that were available from different companies and our above procedure (marked as C&M) as described in FIG. 7. Kit A, Kit B and Kit C were employed following their product protocols and the C&M procedure included alkaline lysis, salting process, PEG fractionation and a silica-based chromatography column. All purified viral solutions were concentrated using Amicon Ultra-4 column filter to yield the resulting solutions in same volumes in PBS, followed by infection in HEK293 cells (A-C), PAGE gel electrophoresis (D) and BCA assay (E). Results from infection are shown as images that are representatives of photos (A). Viral recovery and titer were calculated as shown in histograms that are expressed as mean percentage±SD of GFP cell numbers (B, n=6) and as mean±SD of transducing units (C, n=6) respectively. Results from PAGE gel analysis are shown as images that are representatives of gels (D) and results from BCA assay are shown in histogram that is expressed as mean percentage±SD of protein amount (E, n=6). The purity of AAV viral solutions was calculated to express as mean±SD of transducing units (TU) per pg protein (F, n=6).

A comparative study as example demonstrated the advantages of our new procedure over commercial products. Three of AAV purification kits that are marked as Kit A, Kit B and Kit C were found from the current market, commercially available from different companies. These kits were used for AAV purification from AAV-packaged cells following the product protocols, compared with our present procedure as described above (marked as C&M). Results from infection and protein assays with the resulting viral solutions are shown in FIG. 8, in which we first found that C&M-purified viral solution displayed much higher infectivity (panel A) and >90% viral recovery, while the viral recovery using Kits A, B and C was 27.88±4.82, 6.36±1.27, 4.52±0.66 respectively (panel B); the titer of C&M-purified viral solution is near $10^{10}$ TU/ml, 3-12 times over those of viral solutions purified by commercial kits (panel C), while the later contains much more contaminant proteins than the former (panels D and E). Using the viral transducing units (TU) per pg protein to estimate the viral purity, C&M-purified viral solution shows 149.81±4.60 TU/pg protein, the purity 24-68 times over the viral solutions purified with Kits A-C (FIG. 8 panel F). It is, therefore, concluded that our artistic approach exhibits unparalleled advantages in yielding a high-titer, high-purity AAV solution over the current commercial kits.

Figure 9:
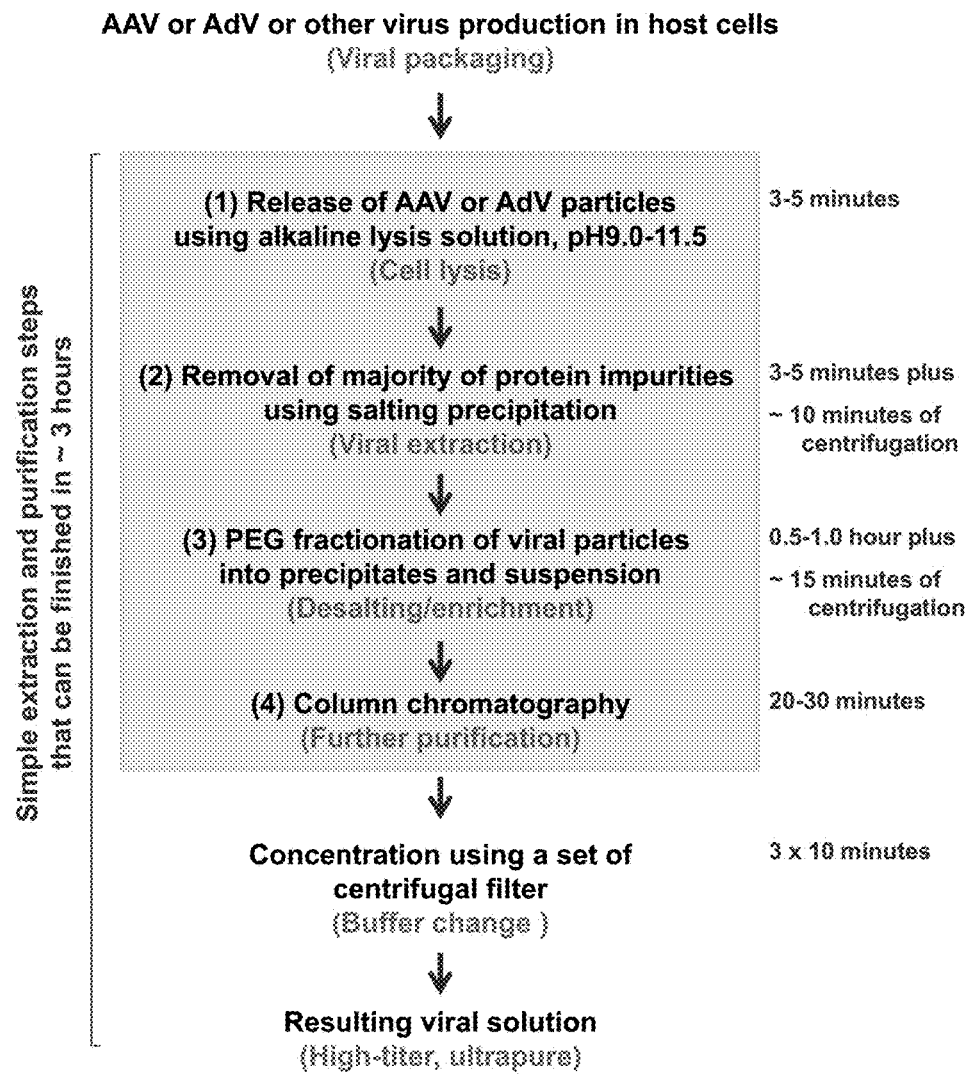
FIG. 9 shows the schematic diagram that outlines the example steps of an approach of one embodiment of the disclosure for purification of AAV and AdV particles. These techniques are suitable for purification of AAV, AdV and any other "naked" viral particles that are packaged within the host cells. The purification procedure includes four primary steps as indicated that can be finished within 3 hours or less: (1) Lysis of the viral packaged cells to release viral particles using an alkaline lysis solution with pH9.0-11.5; (2) Salting precipitation process to remove the majority of host cell protein impurities and retain viral particles in solution using an salting solution; (3) PEG fractionation to separate viral particles into precipitates resulting in desalting, enrichment and further purification of viral particles; (4) Column chromatography to finally purify viral particles, followed by concentration using centrifugal filters, to yield high-titer, ultrapure viral particles. These technologies do not use any toxic compounds for the viral purifications so that the resulting viral solutions can meet the quality requirements for most research purposes and preclinical and clinical trials.

In summary, this study presents a new approach for purification of AAV or AdV particles from their packaged cells, which includes a few important steps as follows (FIG. 9): (1) cell lysis (cell lysates) using an alkaline solution that contains compounds with buffering capability maintaining a pH value of 9.0-11.5; (2) salting precipitation process by adding a salting solution (high salt) to cell lysates to remove the majority of host cell protein impurities in precipitates and retain AAV or AdV viral particles in solutions (viral extracts); (3) PEG fractionation by adding PEG to viral extracts to separate viral particles in precipitates that can be resuspended in an appropriate solution (viral suspensions) and retain protein impurities in solution leading to desalting, enriching and purifying the viral particles; and (4) column chromatography by using silica-based chromatography columns to finally purify the above viral suspensions followed by concentration with centrifugal filters to produce high-titer, ultrapure viral solutions. Moreover, this is a very easy, time-saving procedure that can be finished in about 3 hours and is suitable for purification of all serotypes of AAV or AdV or any other species of packaged viruses retained in host cells. All the solutions used in the procedure do not contain any toxic compounds or reagents so that the resulting viral solutions can meet the quality requirements for most research purposes and/or preclinical and clinical trials.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc., shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A method of extracting viral particles of a recombinant adeno associated virus (AAV) or an adenovirus (AdV) from a sample comprising cells enclosing the viral particles, comprising:

lysing the cells by the addition of an alkaline lysis solution to the sample such that the sample comprises about 0.1% to about 1% of a detergent comprising a salt of deoxycholic acid and has a pH of about 9.5 to about 11 under suitable conditions to lyse the cells; then precipitating proteins released from the lysed cells by adding a salting solution to the sample such that the sample comprises about 0.5 M to about 2.0 M of a salt selected from the group consisting of sodium acetate, potassium acetate and combinations thereof and has a pH of about 4.0 to about 7.0; then removing the precipitated proteins to obtain a supernatant comprising the viral particles; and then precipitating the viral particles by adding a precipitation solution to the supernatant such that the supernatant comprises about 5% to about 12% of a polyethylene glycol (PEG), wherein the method does not include use of ultracentrifugation or freeze-thaw cycles.

2. The method of claim 1, wherein the viral particles are of any one of AAV serotypes 1-11 or any one of AdV species A-G.

3. The method of claim 1, wherein the detergent further comprises sodium dodecyl sulfate (SDS).

4. The method of claim 1, wherein the alkaline lysis solution has a pH of about 9.5 to about 11 and comprises, in addition to the detergent, one or more reagents selected from the group consisting of N-cyclohexyl-3-aminopropanesulfonic acid (CAPS), glycine/sodium, glycine potassium, sodium carbonate, potassium carbonate, sodium phosphate, potassium-phosphate and combinations thereof.

5. The method of claim 1, wherein the salting solution does not include an ammonium salt.

6. The method of claim 1, wherein the PEG has an average molecular weight of about 3000 to about 10000.

7. The method of claim 1, further comprising subjecting the precipitated viral particles to chromatography.

8. The method of claim 7, wherein the chromatography is silica-based chromatography, resin chromatography or ion exchange chromatography columns.

9. The method of claim 1, wherein the method does not include the use of an organic solvent.

10. The method of claim 1, wherein the method does not include the use of affinity chromatography.

* * * * *

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
tctgcaccac cggcaagctg c                                             21

<210> SEQ ID NO 2
<211> LENGTH: 21
<212> TYPE: DNA
<213> ORGANISM: Artificial Sequence
<220> FEATURE:
<223> OTHER INFORMATION: Synthetic

<400> SEQUENCE: 2
gagaagcact gcacgccgta g                                             21

<210> SEQ ID NO 3
<211> LENGTH: 22
<212> TYPE: DNA
<213> ORGANISM: Artificial Sequence
<220> FEATURE:
<223> OTHER INFORMATION: Synthetic

<400> SEQUENCE: 3
ggtctccaac tcctaatctc ag                                            22
```

```
<210> SEQ ID NO 4
<211> LENGTH: 22
<212> TYPE: DNA
<213> ORGANISM: Artificial Sequence
<220> FEATURE:
<223> OTHER INFORMATION: Synthetic

<400> SEQUENCE: 4
aaaatcagaa ggacagggaa gg                                              22

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
ttcctacttg gcagtacatc tacg                                            24

<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6
gtcaatgggg tggagacttg g                                               21
```